United States Patent [19]

Chee

[11] Patent Number: 5,677,157
[45] Date of Patent: Oct. 14, 1997

[54] SOMATIC EMBRYOGENESIS AND TRANSFORMATION OF SQUASH

[75] Inventor: Paula P. Chee, Kalamazoo, Mich.

[73] Assignee: Asgrow Seed Company

[21] Appl. No.: 349,759

[22] Filed: Dec. 5, 1994

Related U.S. Application Data

[63] Continuation of Ser. No. 196,882, Feb. 14, 1994, abandoned, which is a continuation of Ser. No. 854,138, PCT/US90/04692, Aug. 22, 1990, abandoned, which is a continuation of Ser. No. 434,245, Nov. 13, 1989, abandoned, which is a continuation-in-part of Ser. No. 410,527, Sep. 20, 1989, abandoned.

[51] Int. Cl.$^6$ .......................... C12N 15/82; C12N 5/04; A01H 4/00; A01H 5/00
[52] U.S. Cl. .................. 435/172.3; 435/240.45; 435/240.51; 435/240.54; 800/205; 800/DIG. 21
[58] Field of Search .................. 800/205, DIG. 21; 435/240.4, 240.45, 240.54, 320.1, 172.3, 340.51; 536/27, 23.2, 23.7; 935/52, 56, 57, 67

[56] References Cited

U.S. PATENT DOCUMENTS 5,416,011  5/1995  Hinchee et al. .................. 435/172.3

FOREIGN PATENT DOCUMENTS 223452  5/1987  European Pat. Off. .

OTHER PUBLICATIONS

G. An, "Development of Plant Promoter Expression Vectors . . . Tobacco Cells" (1986), Plant Physiol. 81:86–91.
G. An et al, "New Coning Vehicles for Transformation of Higher Plants" (1985), EMBO. J., 4:277–284.
A.R. Anderson et al, "Host Specificity in the Genus Agrobacterium" (1979), Phytopath. 69:320–323.
M.W. Bevan, "Binary Agrobacterium Vectors for Plant Transformation" (1984), Nucl. Acids. Res., 12:8711–8721.
M.W. Bevan, "T–DNA of the Agrobacterium Ti and Ri Plasmids" (1982), Ann. Rev. Genet., 16:357–384.
M.D. Chilton et al, "Stable Incorporation of Plasmid DNA . . . of Crown Gall Tumorigenensis" (1977), Cell. 11:263–271.
M.D. Chilton et al, "Agrobacterium Rhizogenes Inserts . . . Host Plant Root Cells" (1982), Nature 295:432–434.
A. Depicker et al, "Molecular Cloning of Overlapping . . . Endonuclease Mapping" (1980), Plasmid 3:193–211.
A.G. Hepburn et al, "The Use of pNJ5000 as an Intermediate . . . Ti–plasmids" (1985), J. Gen. Microbio. 131:2961–2969.
E.E. Hood et al, "The Hypervirulence of Agrobacterium Tumefaciens . . . Outside of the T–DNA" (1986), J. Bacteriology 168:1291–1301.
R.B. Fry et al, "A Simple and General Method for Transferring Genes Into Plants" (1985), Science 227:1229–1231.
S. Jelaska "Embryoid Formation . . . Hypocotyls in Cucurbita Pepo" (1972), Planta 103:278–280.

S. Jelaska "Rastenje Fragmenata Zrelog Embrija Bundeve Uzgajanih In Vitro" (1973), Acta Bot. Croat. 32:81–94.
S. Jelaska, "Cucurbits", (1986) Biotechnology in Agriculture and Forestry (ed. Y.P.S. Bajai), 2:371–386.
T.M. Klein et al "(High–velocity Microprojectiles . . . Into Living Cells" (1987), Natured 327:70–73.
S. Malepeszy et al "In Vitro Culture of Cucumis Sativus . . . From Callus Formed by Leaf Explants", Z. Pflanzenphysio. Bd. 111 S. 273–276.
V. Moreno et al (1985), Plant Cell Tissue Organ Culture, 5:139–146.
T. Mirashige et al "A Revised Medium for Rapid Growth . . . Tissue Cultures" (1962), Physiol. Plant 15:473–497.
A. Nadolska–Orczyk et al "Cucumber Plant Regeneration . . . Characteristics (1984)", Bulletin Pol. Acad. Sci. 32:423–428.
D.A.C. Pink et al "Rapid Propagation of Cucurbita Pepo L. by Culture of Meristem Tips" (1984) Sci. Hortic. (AMST) 24:107–114.
C.A. Schroder (1968), Bot. Gaz. 129:374–376.
J. Smarrell, Jr. et al "Response of Variious Cucurbits . . . Agrobacterium" (1986), Plant. Physiol. 82:622–624.
A.J. Trulson et al "Transformation of Cucumber . . . Rhizogenes" (1986) Theor. Appl. Genet. 73:11–15.
F. Vilaine et al "Independent Induction of Transformed Roots . . . Agrobacterium Rhizogenes" (1987), Mol. Gen. Genet. 206:17–23.
H. Bohlmann et al "Leaf–specific Thionins of Barley . . . and Possibly Involved . . . Mechanisms of Plants" (1988), EMBO. J. 7:1559–1565.
H.G. Boman et al "Chemical Synthesis and Enzymatic . . . of Cecropins A and B" (1989), Bio. Chem. 264:5852–5860.
H.G. Boman et al "On the Primary Structure of . . . From Hyalophora Cecropia" (1985), Dev. Com. Imm. 9:551–558.
L. Comai et al "Expression in Plants of a Mutant . . . Tolerance to Glyphosate" (1985), Nature 317:741–744.
K.A. Daher et al "Isolation and Characterization of Human Defensin cDNA Clones" (1988), Proc. Natl. Acad. Sci. USA 85:7327–7331.
G. della–Cioppa et al "Targeting a Herbicide–resistant Enzyme . . . of Higher Plants" (1987), Bio. Tech. 5:579–584.
M. Cuozzo et al "Viral Protection in Transgenic Tobacco . . . or Its Antisense RNA" (1988), Bio. Tech. 6:549–557.
S.C. Falco et al "Molecular Biology of Sulfonylurea Herbicide Activity" (1985), Biotechnology in Plant Sciences (Academic Press, Inc., New York, NY) pp. 313–328.

(List continued on next page.)

*Primary Examiner*—David T. Fox
*Attorney, Agent, or Firm*—Fitzpatrick, Cella, Harper & Scinto

[57] ABSTRACT

A method involving somatic embryogenesis of various squash (*Cucurbita pepo L.*) tissues is described which can be used for the regeneration of normal squash plants. This method is also used for the transfer and integration of genetic materials into the genome of squash plants, which belong to the family Cucurbitaceae, followed by regeneration of such transformed plants. Thus regenerated transformed whole squash plants are produced by this method.

12 Claims, No Drawings

OTHER PUBLICATIONS

D. Hultmark et al "Insect Immunity: Attacins, a Family . . . From Hyalophora Cecropia" (1983), EMBO J. 2:571–576.

R.A. Jefferson et al "Gus Fusions . . . Gene Fusion Marker in Higher Plant" (1987), EMBO. J. 6:3902:3907.

K.Y. Lee et al (1988), EMBO. J. 7:1241–1248.

B.J. Mazur et al "Sequence of a Genomic DNA Clone . . . From Tobacco" (1985), Nucl. Acid. Res. 13:2373–2386.

M. Pietrzak et al "Expression in Plants of Two Bacterial . . . Plant Expression Vector" (1986), Nuc. Acids. Res. 14:5857–5868.

P. Powell–Abel et al "Delay of Disease Development . . . Mosaic Virus Coat Protein Gene" (1986), Science 232:738–743.

J.J. Sanchez–Serrano et al "Wound–induced Expression of a Potato . . . transgenic Tobacco Plants" (1987), EMBO. J. 6:303–307.

H.E. Schnepf et al "The amino Acid Sequence of a Crystal Protein . . . Base Sequence" (1985), J. Biol. Chem. 260:6264–6272.

V. Sekar et al "Molecular Cloning and Characterization . . . Var. Tenebrionis" (1987), Proc. Natl. Acd. Sci. USA 84:7036–7040.

D.M. Shah et al "Engineering Herbicide Tolerance in Transgenic Plants" (1986), Science 233:478–481.

D.M. Stalker et al "A Single Amino Acid Substitution . . . Synthase Confers Resistance to the Herbicide Glyphosphate" (1985), J. Bio. Chem. 260:4724–4728.

M. Vaeck et al "Transgenic Plants Protected From Insect Attack" (1987) Nature 328:33–37.

C. Waalwijk et al "Molecular Cloning and the Nucleotide Sequence . . . Supsp. Israelensis" (1985), Nucl. Acids. Res. 13:8207–8217.

M. Zasloff "Magainins, a Class of Antimicrobial Peptides . . . Sequence of a Precursor" 1987, Proc. Natl. Acad. Sci. USA 84:5449–5453.

Jelaska, S., "Cucurbits" & Biotechnology in agriculture and forestry 2. Crops I (edited by Bajaj, Y.P.S.)., Berlin; Springer–Verlag, 1986, pp. 371–386, 485–519, many ref. in English (JA: 8703); Commonwealth Agricultural Bureau, 871657363 CAB, Quest Acc. No. 87245434.

Jelasca, Sibila: "Induction of embryogenic callus in Cucurbita pepohypocolyl explants by indole–3–ethanol and its sugar conjugates", see p. AB–819, abstract 89878, & Physiol. Plant 64(2): 237–242, 1985, Biological Abstracts, vol. 80, 1985.

Jelaska, Sibila: "Embryogenesis and organogenesis in pumpkin explant", see page 1120, abstract 10484 & Physiol. Plant 31(4): 257–261, illus. 1974, Biological Abstracts, vol. 49, No. 2, 1985.

Smarrelli, J., Jr., et al: "Response of various cucurbits to infection by plasmid harboring strains of agrobacterium" & Dep. Biol., Loyola Univ. Chicago, Illinois 60626, USA, Plant Physiciology, vol. 82, No. 2, 1986, pp. 622–624, 17 Ref. in English (JA: 8701), Commonwealth Agricultural Bureau, 861655509 CAB, Quest Acc. No. 86482970.

Vaulx, R.D., et al: "Obtention of embryos and plants from in vitro culture of unfertilized ovules of cucurbita pepo", & Genetic manipulation in plant breeding. Proceedings international symposium organized by Eucarpia, Sep. 8–13, 1985, Berlin (West), Germany, Walter de Gruyter, 1986, pp. 295–297. 8 ref in English, (JA:05), Commonwealth Agricultural Bureau, 871658967 CAB, Quest Acc. No. 87251406.

SOMATIC EMBRYOGENESIS AND TRANSFORMATION OF SQUASH

CROSS REFERENCE TO RELATED APPLICATIONS

The present application is a continuation of application Ser. No. 08/196,882 filed Feb. 14, 1994, abandoned, which is a continuation of application Ser. No. 07/854,138 filed Mar. 18, 1992, abandoned, which is a continuation of International Application No. PCT/US90/04692 filed Aug. 22, 1990 designating the United States, abandoned, which is a continuation of application Ser. No. 07/434,245 filed Nov. 13, 1989, abandoned, which is a continuation-in-part of application Ser. No. 07/410,527, filed Sep. 20, 1989, abandoned.

FIELD OF INVENTION

The present invention relates to a regeneration method for squash (*Cucurbita pepo L.*) and the use of the sources of regenerable tissue for the transfer of genetic material. More specifically, the invention relates to a process for preparing squash tissues, obtaining somatic embryos, and regenerating these embryos into normal squash plants. This invention also provides for the transfer of genetic material into squash embryos for the purpose of producing transformed plant cells and transformed squash plants which are resistant to plant viruses, insects, weeds, pathogenic microbes and to obtain other beneficial traits as a result of the transfer of genetic information.

BACKGROUND OF THE INVENTION

Squash (*Cucurbita pepo L.*) is an important crop in many regions of the temperate zones of both hemispheres, and improvement in the ability of this crop to resist viruses, insects, weeds, and to improve its growth and vigor would be of considerable commercial value. Present plant breeding programs have made considerable improvements to this species with respect to these characteristics; however, it is believed that these characteristics could be made more rapidly with the development of cellular events such as tissue culture regeneration and molecular events such as the transfer of genetic material.

The regeneration of cucurbit species from tissue cultures has been reported for cucumber (*Cucumis sativas L.*) (Nadolska-Orczyk and Malepszy, 1984) and melon (*Cucumis melo L.*) Moreno et al, (1985). Schroder (1968) reported the production of embryogenic tissue from pericarp tissues of squash. Jelaska (1972, 1973) reported somatic embryogenesis in hypocotyl and cotyledon-derived callus of pumpkins and demonstrated that embryos could develop into normal plants. Pink and Walkey (1984) reported a rapid propagation method for pumpkin through apical meristem culture. However, the literature contains no reports on whole plant regeneration of squash, while we describe here two methods for the efficient regeneration of squash. These regeneration methods also provide the material which can be utilized for the transfer of genetic material into the squash genome.

One method for the transfer of genetic information into the genomes of dicotyledonous plants involves the use of two pathogenic species of Gram-negative soil bacteria, *Agrobacterium tumefaciens* and *Agrobacterium rhizogenes* (see review by Bevan and Chilton, 1982) which results in the diseases known as Crown Gall and Hairy Root, respectively. In each of these diseases the causative agent has been identified as resulting from the transfer and integration of a segment of the large pTi or pRi DNA plasmid, known as the T-DNA regions (Chilton et al., 1977; Chilton et al., 1982). The identification of several common steps in the pTi and pRi T-DNA transfer mechanism and the genes contained within these T-DNA regions which are responsible for the disease has resulted in the engineering of avirulent Agrobacterium strains (Hepburn et al., 1985; Hood et al., 1986; Vilaine and Casse-Delbart, 1987). This information has also led to the construction of smaller, wide-host-range, plasmids which are capable of replication in both *E.coli* and Agrobacterium strains. Such plasmids contain the Agrobacterium-derived pTi or pRi DNA signals necessary for the transfer of an engineered T-DNA region from the bacteria into plant cells. These plasmids are referred to as binary plasmids (Bevan, 1984; An et al., 1985).

Many of the species belonging to the family Cucurbitaceae are known to be susceptible to infection by these Agrobacterium pathogens (see review by Anderson and Moore, 1979; Smarrelli et al., 1986). Regeneration of squash (*Cucurbita pepo L.*) is described below. The combination of these two facts suggests that Agrobacterium-mediated transfer of genetic information into the genome of cucurbit species (such as *Cucurbita pepo L.*) should be readily achievable.

In addition to the use of Agrobacterium-mediated transformation of regenerable plant tissues a second method for gene transfer has recently been developed: the use of microprojectiles to transfer DNA molecules into plant cells (Klein et al., 1987). The method (described below) for the regeneration of squash provides tissues which can be readily transformed by the microprojectile procedure. The development of regeneration and transformation systems for the transfer and stable integration of genetic material into the genome of cucurbit species (cucumber, melon, and squash) will be useful for the transfer of genetic traits which are difficult or impossible to transfer via conventional plant breeding techniques.

The development of gene transfer technology for cucurbit species (such as squash) will be used to transfer engineered genes which will: confer resistance to viral infection (Powell-Able et al., 1986; Cuozzo et al., 1988), herbicide resistance (Comai et al., 1985; della-Cioppa et al., 1987; Lee et al., 1988; Stalker et al., 1985), or any other useful genetic traits such as genes for resistance to insect pests, microbes and other pests, see examples listed below.

INFORMATION DISCLOSURE

The transformation and regeneration of transformed cucumber plants which express the NPT II gene has been previously reported by Trulson et al. (1986). This transformation was achieved using *Agrobacterium rhizogenes*. European patent application EP O 223 452 describes plants that are resistant to vital diseases and methods for producing them. PCT patent application PCT/US86/00614 refers generally to a method of conferring resistance to parasite to a host of the parasite. There are also other patents for herbicide and use of proteins to obtain resistance to microbes.

An, G. (1986), Development of plant promoter expression vectors and their use for analysis of differential activity of nopaline synthase promoter in transformed tobacco cells. Plant Physiol. 81:86–91.

An, G., Watson, B. D., Stachel, S., Gordon, M. P., and Nester, E. W. (1985), New cloning vehicles for transformation of higher plants. EMBO J. 4:277–284.

Anderson, A. R. and Moore, L. W. (1979), Host specificity in the genus Agrobacterium. Phytopath. 69:320–323.

Bevan, M. W. (1984), Binary Agrobacterium vectors for plant transformation. Nucl. acids Res. 12:8711–8721.

Bevan, M. W. and Chilton, M.-D. (1982), T-DNA of the Agrobacterium Ti and Ri plasmids. Ann. Rev. Genet. 16:357–384.

Chilton, M.-D., Drummond, M. H., Merlo, D. J., Sciaky, D., Montoya, A. L., Gordon, M. P., and Nester, E. W. (1977), Stable incorporation of plasmid DNA into higher plant cells: the molecular basis of crown gall tumorigenesis. Cell 11:263–271.

Chilton, M.-D., Tepfer, D. A., Petit, A., David, C., Casse-Delbart, F., Tempe, J. (1982), *Agrobacterium rhizogenes* inserts T-DNA into the genomes of the host plant root cells. Nature 295:432–434.

Depicker, A., Dewilde, M., DeVos, G., Van Montagu, M., and Schell, J. (1980), Molecular cloning of overlapping segments of the nopaline Ti-plasmid pTIC58 as a means to restriction endonuclease mapping. Plasmid 3:193–211.

Hepburn, A. G., White, J., Pearson, L., Maunders, M. J., Clarke, L. E., Prescott, A. G., and Blundy, K. S. (1985), The use of pNJ5000 as an intermediate vector for genetic manipulation of Agrobacterium Ti-plasmids. J. Gen. Microbio. 131:2961–2969.

Hood, E. E., Helmet, G. L., Fraley, R. T., and Chilton, M.-D. (1986), The hypervirulence of *Agrobacterium tumefaciens* A281 is encoded in a region of pTiBo542 outside of the T-DNA. J. Bacteriology 168:1291–1301.

Horsch, R. B., Fry, J. E., Hoffmann, H. L., Eichholtz, D., Rogers, S. G., and Fraley, R. T. (1985), A simple and general method for transferring genes into plants. Science 227:1229–1231.

Jelaska, S. (1972), Planta 103:278–280.

Jelaska, S. (1973), Acta Bot. Croat. 32:81–94.

Jelaska, S. (1986), Cucurbits, In: Biotechnology in Agriculture and Forestry (ed. Y. P. S. Bajai) 2:371–386.

Klein, T. M., Wolf, E. D., and Sanford, J. C. (1987), "High-velocity microprojectiles for delivering nucleic acids into living cells", Nature 327:70–73.

Malepepsy, S. and Nadolska-Orczyk, A. (1983), "In vitro Culture of *Cucumis staivus* I. Regeneration of plantlets from callus formed by leaf explants", Z. Pflanzenphysio. Bd. 111 S. 273–276.

Moreno, V., Garcia-Sogo, M., Granell, I., Garcia-Sogo, B., and Rorg, L. A. (1985), Plant Cell Tissue Organ Culture 5:139–146.

Murashige, T. and Skoog, S. (1962), A revised medium for rapid growth and bioassays with tobacco tissue cultures, Physiol. Plant 15:473–497.

Nadolska-Orczyk, A. and Malepszy, S. (1984), Cucumber plant regeneration from leaf explants-selected characteristics, Bulletin Pol. Acad. Sci. 32:423–428.

Pink, D. A. C. and Walkey, D. G. A. (1984), Sci. Hortic. (AMST) 24:107–114.

Schroder, C. A. (1968), Bot. Gaz 129:374–376.

Smarrelli, Jr., J., Watters, M. T., and Diba, L. (1986), Response of various cucurbits to infection by plasmid-harboring strains of Agrobacterium, Plant. Physiol. 82:622–624.

Trulson, A. J., Simpson, R. B., and Shahin, E. A. (1986), "Transformation of cucumber (*Cucumis sativus L.*) plants with *Agrobacterium rhizogenes*", Theor. Appl. Genet. 73:11–15.

Vilaine, F. and Casse-Delbart, F. (1987), Independent induction of transformed roots by the TL and TR regions of the Ri plasmid of agropine type *Agrobacterium rhizogenes*, Mol. Gen. Genet. 206:17–23.

The following scientific publications are of interest but not relevant:

Bohlmann, H., Clausen, S., Behnke, S., Giese, H., Hiller, C., Reimann-Philipp, U., Schrader, G., Barkholt, V., and Apel, K. (1988), Leaf-specific thionins of barley-a novel class of cell wall proteins toxic to plant-pathogenic fungi and possibly involved in the defense mechanism of plants, EMBO J. 7:1559–1565.

Boman, H. G., Boman, I. A., Andreu, D., Li, Z.-q., Merrifield, R. B., Schlenstadt, G., and Zimmermann, R. (1989), Chemical synthesis and enzymatic processing of precursor forms of Cecropins A and B. J. Bio. Chem. 264:5852–5860.

Boman, H. G., Faye, I., v.Hofstein, P., Kockum, K., Lee, J.-Y. Xanthopoulos, K. G., Bennich, H., Engstrom, A., Merrifield, R. B., and Andreu, D. (1985), On the primary structure of lysozyme, cecropins, and attacins from *Hyalophora cecropia*. Dev. Com. Imm. 9:551–558.

Comai, L., Facciotti, D., Hiatt, W. R., Thompson, G., Rose, R. E., and Stalker, D. M. (1985), Expression in plants of a mutant aroA gene from *Salmonella typhimurium* confers tolerance to glyphosate, Nature 317:741–744.

Daher, K. A., Lehrer, R. I., Ganz, T., and Kronenberg, M. (1988), Isolation and characterization of human defensin cDNA clones, Proc. Natl. Acad. Sci. USA 85:7327–7331.

della-Cioppa, G., Bauer, S. C., Taylor, M. L., Rochester, D. E., Klein B. K., Shah, D. M., Fraley, R. T., and Kishore, G. M. (1987), Targeting a herbicide-resistant enzyme from *Escherichia-coli* to chloroplasts of higher plants, Bio/Tech. 5:579–584.

Cuozzo, M., O'Connell, K., Kaniewski, W., Fang, R.-X., Chua, N.-H., and Tumer, N. E., (1988), Viral protection in transgenic tobacco plants expressing the cucumber mosaic virus coat protein or its antisense RNA, Bio/Tech. 6:549–557.

Falco, S. C., Chaleff, R. S., Dumas, K. S., LaRossa, R. A., Leto, K. J., Mauvais, C. J., Mazur, B. J., Ray, T. B., Schloss, J. V., and Yadav, N. S. (1985), Molecular biology of sulfonylurea herbicide activity. In: Biotechnology in Plant Sciences (Academic Press, Inc. New York, N.Y.) pp 313–328.

Hultmark, D., Engstrom, A., Anderson, K., Steiner, H., Bennich, H., and Boman, H. G. (1983), Insect immunity: attacins, a family of antibacterial proteins from *Hyalophora cecropia*. EMBO J. 2:571–567.

Jefferson, R. A., Kavanagh, T. A., Bevan, M. W. (1987), Gus fusions: β-glucuronidase as a sensitive and versatile gene fusion marker in higher plant, EMBO J. 6:3901–3907.

Lee, K. Y., Townsend, J., Tepperman, J., Black, M., Chui, C. F., Mazur, B., Dunsmuir, P., and Bedbrook, J. (1988), EMBO J. 7:1241–1248.

Mazur, B. J. and Chui, C.-F. (1985), Sequence of a genomic DNA clone for the small subunit of ribulose bis-phosphate carboxylase-oxygenase from tobacco, Nucl. Acid. Res. 13:2373–2386.

Pietrzak, M., Shillito, R. D., Hohn, T., and Potrykus, I., (1986), Expression in plants of two bacterial antibiotic resistance genes after protoplast transformation with a new plant expression vector, Nuc. Acids. Res. 14:5857–5868.

Powell-Abel, P., Nelson, R. S., De, B., Hoffman, N., Rogers, S. G., Fraley, R. T., and Beachy, R. N. (1986), Delay of disease development in transgenic plants that express the tobacco mosaic virus coat protein gene, Science 232:738–743.

Sanchez-Serrano, J. J., Keil, M., O'Connor, A., Schell, J., and Willmitzer, L. (1987), Wound-induced expression of a potato proteinase inhibitor II gene in transgenic tobacco plants, EMBO J. 6:303–307.

Schnepf, H. E., Wong, H. C., and Whiteley, H. R. (1985), The amino acid sequence of a crystal protein from *Bacillus thuringiensis* deduced from the DNA base sequence, J. Biol. Chem. 260:6264–6272.

Sekar, V., Thompson, D. V., Maroney, M. J., Bookland, R. G., and Adang, M. J. (1987), Molecular cloning and characterization of the insecticidal crystal protein gene of *Bacillus thuringiensis* var. *tenebrionis*,. Proc. Natl. Acad. Sci. USA 84:7036–7040.

Shah, D. M., Horsch, R. B., Klee, H. J., Kishore, G. M., Winter, J. A., Turner, N. E., Hironaka, C. M., Sanders, P. R., Gasser, C. S., Aykent, S., Siegel, N. R., Rogers, S. G., and Fraley, R. T. (1986), Engineering herbicide tolerance in transgenic plants, Science 233:478–481.

Stalker, D. M., Hiatt, W. R., and Comai, L. (1985), A single amino acid substitution in the enzyme 5-enolyruvylshikimate-3-phosphate synthase confers resistance to the herbicide glyphosate, J. Bio. Chem. 260:4724–4728.

Vaeck, M., Reynaerts, A., Hofte, H., Jansens, S., De Beuckeleer, M., Dean, C., Zabeau, M., Van Montagu, M., and Leemans, J., (1987), Transgenic plants protected from insect attack, Nature 328:33–37.

Waalwijk, C., Dullemans, A. M., van Workum, M. E. S., and Visser, B. (1985), Molecular cloning and the nucleotide sequence of the $M_r 28000$ crystal protein gene of *Bacillus thuringiensis* supsp. *israelensis*. Nucl. Acids Res. 13;8207–8217.

Zasloff, M. (1987), Magainins, a class of antimicrobial peptides from Xenopus skin: isolation, characterization of two active forms, and partial cDNA sequence of a precursor, Proc. Natl. Acad. Sci. USA 84:5449–5453.

SUMMARY OF THE INVENTION

This invention provides:

A method of transforming and regenerating squash, which belong to the family Cucurbitaceae, which comprises (1) excising squash tissue selected from the group consisting of shoot tips from germinating squash seeds and squash tissue from mature seeds, (2) producing transformed embryogenic calli from said tissues, (3) selectively growing the transformed embryogenic calli on media containing kanamycin, and (4) subjecting the transformed embryogenic calli to an embryogenic regeneration procedure from which whole transformed squash plants can be obtained.

When the excised tissue is shoot tips from germinating squash seed, the transformed embryogenic calli is produced by (a) inoculating said excised squash tissue with virulent or avirulent strains of Agrobacterium and (b) culturing the resulting explants on Shoot Explant Induction Medium comprising Ms media, 2,4,5-T, BAP, Kn.

When the excised tissue is tissue from mature squash seed, the transformed embryogenic calli is produced by (a) inoculating said excised squash tissue with virulent or avirulent strains of Agrobacterium and (b) culturing the resulting explants on Seed Explant Induction Medium comprising MS media, 2,4-D or 2,4,5-T, BAP, Kn.

DETAILED DESCRIPTION OF THE INVENTION

In general the process of this invention involves the steps schematically shown in Chart 1.

Formation and Regeneration of Embryonic Squash Calli

Method 1 Somatic embryos derived from shoot tip explants

Plant Material

Seeds of summer squash (*Cucurbita pepo L.*) cv. YC 60 were obtained from the Asgrow Seed Co., Kalamazoo, Mich. and they were soaked in tap water for approximately 15 minutes and then their seed coats were removed by hand. The de-coated seeds were treated with 95% alcohol for two minutes followed by immersion in a 25% (v/v) solution of commercial hypochlorite (Clorox, which contains 5.25% sodium hypochlorite) for 25 minutes and then rinsed four times with sterile distilled water. Sterilized seeds were placed in Magenta boxes with 50 ml of Murashige and Skoog (1962) (MS) basal medium containing 30 g/l sucrose, 8 g/l Difco agar (Difco Laboratories). The seeds were germinated in a Percival incubator at 28° C. in darkness.

Induction of Somatic Embryogenesis and Plant Regeneration

Shoot apices consisting of the apical domes and some supporting tissue were excised from seven-day old in vitro grown seedlings. The apices were cut into longitudinal halves and cultured horizontally on Shoot Explant Induction Medium, e.g., containing 1.2 mg/l 2,4,5-T and 0.8 mg/l BAP, optionally supplemented with 0.1 mg/l NAA. All tissue culture media were supplemented with 3% sucrose and solidified with 0.8% Phytagar (Gibco). The pH of the media was adjusted to 5.8 prior to being autoclaved at 121° C. for 20 minutes. All subsequent tissue cultures were maintained in darkness at 28° C. After two weeks of culturing on this medium, the shoot tip explants became swollen. The tissue lost its green color and became amber. Embryogenic callus tissues were propagated by successive subculturing of the slimy, translucent callus tissue onto plates containing fresh Shoot Explant Induction Medium supplemented with NAA, every week. After six weeks, the callus tissue propagated appeared shiny, translucent and slimy. Following eight weeks of incubation using the above conditions, putative somatic embryos were observed to organize from sectors on the surface of the slimy callus. To promote further development of the putative somatic embryos, they were transferred to Conversion Medium, comprising MS medium plus 0.05 mg/l NAA and 0.05 mg/l kinetin. These structures were maintained on this medium at 28° C. under diffuse cool-white fluorescent lamps (4 klx) with a 16-hour photoperiod. Within three weeks, shoot-tips of the embryos became green and plantlets were obtained three weeks later. About 75% of somatic embryos developed into whole plants. A superficial evaluation revealed that regenerated plants displayed no gross phenotypic abnormalities. Regenerated plants flowered and set seed.

Method 2 Somatic embryos derived from mature seeds.

Plant material

Mature seeds of summer squash, *Cucurbita pepo L.* cv. YC 60, were obtained from the Asgrow Seed Company, Kalamazoo, Mich. The seeds were surfaced sterilized for 10 minutes with a 15% (v/v) solution of Clorox (commercial bleach containing 5.25% sodium hypochlorite) and rinsed three times with sterile water. The seed coats were removed manually and the seeds sterilized again with 25% Clorox for 25 minutes, rinsed three times with sterile water, following by 70% alcohol for one minute and rinsed three more times with sterile water.

Induction of Somatic Embryogenesis and Plant Regeneration (A) Sterilized seeds were cut transversely into two unequal sections: one section containing the embryonic axis and one-third of the cotyledon and the other section containing two-thirds of the cotyledon. The explants containing the embryonic axis were cultured at 26° C., in darkness, with the cut surface facing up, and the explants containing only the cotyledons were cultured horizontally on Seed Explant Induction Medium, e.g., containing a factorial combination of eight concentrations of 2,4-D (0.5, 1, 2, 3, 5, 10, 25, 50 mg/l) and five concentrations of kn (0, 0.5, 1.2, 3 mg/l), after nine weeks with one subculture, the embryogenic callus tissue containing putative somatic embryos were formed on the surface of explants. These somatic embryos were transferred to Conversion Medium. These structures were maintained on this medium at 28° C. under diffuse cool-white fluorescent lamps (4 klx) with a 16-hour photoperiod. As soon as the apical regions displayed development, the plantlets were transferred to Magenta boxes containing one-half strength MS basal medium. After plantlets developed a root system, they were transferred to potting mix and covered with a ZIPLOC storage bag for hardening-off. Subsequently, the hardened plants were transplanted to soil and grown to maturity in a greenhouse. Regenerated plants displayed no gross phenotypic abnormalities, flowered and set seeds which were viable and produced subsequent generations.

B. Explants were cultured on Seed Explant Induction Medium, e.g., containing a factorial combination of three concentrations of IAA (0, 1.5 and 3 mg/l) and five concentrations of kn (0, 1.5, 3.0, 4.5 and 6.0 mg/l). After nine weeks with one subculture, the tissues were scored for embryogenic callus formation.

C. The explants were cultured on Seed Explant Induction Medium, e.g., containing 1.2 mg/l 2,4,5,-T, 0.8 mg/l BAP and 0.1 mg/l kn at 26° C. in darkness. After nine weeks with one subculture, the embryogenic callus tissues containing putative somatic embryos that formed on the surface of the explants were transferred to conversion medium and incubated under diffuse cool white fluorescent lamps (4 klx) with a sixteen-hour photoperiod. Subsequent procedures were followed as described in experiment 1.

Abbreviations:
BAP=6-benzylaminopurine,
2,4-D=2,4-dichlorophenoxyacetic acid,
IAA=indoylbutyric acid,
NAA=naphthylacetic acid,
2,4,5-T=2,4,5-trichlorophenoxcyacetic acid,
Kn=kinetin
MS=Murashige and Skoog (1962).

Transformation Procedures

Example 1 The use of Agrobacteria for transformation

Transformation of squash tissues, derived either from the shoot tips or freshly cut mature seeds was done using methods similar to those described by Horsch et al. (1985). Shoot apices consisting of the apical domes and some supporting tissues were removed aseptically from young squash seedlings and they were submerged in an overnight culture of either the avirulent Agrobacterium strain C58Z707 (Hepburn et al., 1985), virulent strain C58 (Depicker et al., 1980) or any other strains of *Agrobacterium tumefaciens* or *rhizogenes*. In addition, squash tissues derived from freshly cut mature seeds and are subjected to transformation by Agrobacterium in a similar manner. Agrobacterium strains should contain a binary plasmid, such as, pGA482 (An et al., 1985; An, 1986) which has been modified (see examples) to contain a beneficial gene(s) for transfer and integration into the squash genome. After gentle shaking to ensure that all edges were infected, the plant tissues were blotted dry and cultured abaxial side down in a sterile petri dish containing 10 ml of Shoot Explant Induction Medium consisting of MS basal medium supplemented with 1.2 mg/l of 2,4,5-T; 0.8 mg/l of BAP; 0.1 mg/l of kinetin) as described above, followed by growth in the dark at 26° C. Tissues derived from mature seeds would be treated Seed Explant Induction Medium consisting of MS medium containing 5 mg/l 2,4-D or 1.2 mg/l 2,4,5-T and 0.8 mg/l BAP and 0.1 mg/l kinetin. After four days, the Agrobacterium-infected tissues are transferred to petri plates containing the same medium supplemented with 500 µg/ml carbenicillin and between 100 to 200 µg/ml kanamycin and cultured for six additional weeks in the dark at 28° C. In cases where Agrobacterium overgrowth was a problem, the tissues were rinsed with MS salt containing 500 µg/ml carbenicillin prior to transferring to subsequent petri plates.

Regeneration of potentially transformed squash callus tissues was done according to the respective procedures described above in the embodiments of the invention. After incubation for about nine weeks (two to three subcultures) characteristic gel like callus formed at the surface of the squash tissues. Embryogenic calli containing putative somatic embryos were excised and placed on Conversion Medium (this medium is identical for both squash tissue sources) supplemented with 100 to 200 µg/ml of kanamycin sulfate; 500 mg/l of carbenicillin and grown under a 16-hour photoperiod using 2 klx of cool white light. As soon as the apical regions displayed development, the plantlets were transferred to magenta boxes containing one-half strength MS basal medium. After plantlets developed a root system, they were transferred to potting mix. Plants regenerated in this manner displayed no gross phenotypic abnormalities. They flowered and set seeds which produced subsequent generations.

Example 2 The use of microprojectiles for transformation

Squash somatic embryos derived from squash shoot tips are obtained as described in the embodiment of the invention (using, e.g., Shoot Explant Induction Medium containing 1.2 mg/l of 2,4,5-T; 0.8 mg/l BAP; 0.1 mg/l of kinetin). In addition, squash somatic embryos can be obtained from mature squash seeds as described in the invention (using, e.g., Seed Explant Induction Medium containing 5 mg/l 2,4-D or 1.2 mg/l 2,4,5-T and 0.8 mg/l BAP and 0.1 mg/l kinetin). These embryo tissues were bombarded with microprojectiles which have been coated with DNA containing a plasmid encoding a beneficial gene(s), as described by the manufacturer. After bombardment these tissues were allowed to grow for two days on these plates followed by transfer to plates containing the respective fresh media. If the DNA construction used contained the plant expressible NPT II gene, the selection drug, kanamycin 100 to 200 mg/ml was added to the fresh plates. Squash tissues bombarded with microprojectiles were regenerated using the procedures described above (depending on the original tissue source) in the embodiment of the invention.

The Transfer of Useful Genetic Material

Example 3 The transfer of virus coat protein genes

The purpose of this example is to generate a construction for the expression of a plant virus coat protein gene which, when expressed in a plant, results in reduced symptoms or resistance to later infections by that virus. In general, after the identification of a coat protein gene by nucleotide sequencing, its sequences can be modified by using specific oligomers and the technique referred to as polymerase chain reaction (PCR), to attach specific restriction enzyme sites to any coat protein gene. These restriction enzyme sites can be used to clone the coat protein gene into a plant expression vector which contains the necessary gene regulatory elements needed for controlling expression of the gene after transfer into the genome of various plants. A scheme describing the use of the plant expression vector p18UCcpexp for the cloning of various coat protein genes is shown in Chart 2. To facilitate Agrobacterium-mediated gene transfer the plant expressible coat protein is cloned into a binary vector and to facilitate microprojectile-mediated gene transfers a marker gene such as the β-glucuronidase gene (Jefferson, et al. 1987) is attached to the plasmid. (see Chart 2).

Plants that are resistant to virus diseases and methods for producing them are described in EP 223,452, and in Patent Application PCT/US89/03288, published Mar. 8, 1990, entitled "Cucumber Mosaic Virus Coat Protein Gene", and Patent Application PCT/US89/03094 published Mar. 8, 1990, entitled "Potyvirus Coat Protein Genes and Plants Transformed Therewith". The use of viral coat protein genes to obtain resistance in transgenic plants has been described by Powell-Abel et al (1986). Viral coat protein genes are isolated from any number of plant virus classes (tobamo, cucumo, poty, tobra, AMV, etc.) and expressed constitutively in plants after the attachment of the CaMV promoter and downstream 3' plant polyadenylation signals.

The construction of plant expressible coat protein genes is described in Examples 3 and 4 and accompanying charts of Application PCT/US89/03288 and in Examples 8, 11 and 14 and accompanying charts of Application PCT/US89/03094. These Examples and accompanying charts are herein incorporated by reference.

Example 4 Transfer of Herbicide Resistance Gene

This example illustrates how to generate plant expressible genes which allow a plant to be resistant to specific classes of herbicides. Such plants are useful for several reasons: (1) herbicides normally lethal can be used, and (2) different crops can be used in close rotations on soil which may contain residual amounts of a previously used herbicide that is normally lethal to the second crop. Two genes of interest are mutant derivatives (derived from plant or bacterial sources) of the acetolactate synthase (ALS) gene which are not sensitive to chlorsulfuron and sulfometuron methyl herbicides (Falco et al., 1985) and mutants of the gene encoding enolpyruvylshikimate-3-phosphate synthase (EPSPS) (Stalker et al., 1985) which are not sensitive to the herbicide glyphosate.

A gene which encodes an important enzyme which is either resistant to or detoxifies a specific herbicide is cloned downstream from a plant promoter, such as: CaMV 35S (Pietrzak et al, 1986), ribulose-1,5-biphosphate carboxylase small subunit gene (Mazur and Chui, 1985) or other strong plant gene promoter and upstream from a plant gene poly (A) signal sequence (see Chart 3).

This gene is then cloned into an Agrobacterium-derived vector (either binary or cis) and using the above-described plant transformation methods this genetic material can be transferred and integrated into the squash genome (Chart 3). This gene can also be cloned into a vector containing a plant expressible marker gene (Chart 3) and transferred into squash plants using the microprojectile-mediated gene transfer method (see Example 2).

Example 5 Transfer of Insect-Resistance Genes

In nature, numerous polypeptides exist which are toxic to insects and nematodes. The best known protein toxins are those associated with different strains *Bacillus thuringiensis;* for example, *B. israelenis* is active against Diptera (mosquitoes and blackflies), *B. Thuringiensis* is active against Lepidoptera, and *B. san diego* is active against Colioptera. The toxin protein found in each of these bacteria is highly specific to insect pests; they are not toxic to other organisms. Thus, the transfer and expression of genes encoding such toxic proteins in plants are beneficial in reducing insect damage without using chemical insecticides thereby avoiding risk to other organisms. The genes encoding many of these toxic proteins have been isolated and sequenced (Schmeph et al., 1985; Waalwijk et al., 1985; Sekar et al., 1987). The transfer of the *B. thuringiensis* toxin gene into tobacco and its usefulness in protecting the plant from insect damage has been reported by Vaeck et al. (1987). Thus, the combination of using the regeneration and transformation systems described here and plant expressible Bacillus toxin genes (Chart 4) allows for the transfer of a useful genetic trait to squash (see Examples 1 and 2 for gene transfer methods).

Example 6 Transfer of Antimicrobial Gene

This example is to illustrate how to generate plant expressible genes which allow a plant to be resistant to infections by bacteria and fungi. In nature, several classes of polypeptides have been isolated and found to convey broad-spectrum antimicrobial activity; for example, magainins (Zasloff, 1987), defensins (Daher et al., 1988), lysozymes (Boman et al., 1985), Cecropins (Boman et al., 1989), attacins (Haltmark et al., 1983), thionins (Bohlmann et al., 1988), and the like. Genes encoding these antimicrobial peptides or their more active modified forms can be synthesized and engineered for expression in plants. Promoters for the expression of these antimicrobial polypeptide genes can include the constitutive type or others which have tissue specificity. The use of tissue specific promoters, or wound inducible promoters (Sanchez-Serrano et al., 1987) would be useful so as to produce the antimicrobial peptide only when it is needed or in tissues which are more vulnerable to attack by bacterial or fungi, or both pests. Thus the engineering of genes encoding antimicrobial polypeptide genes combined with the plant transformation and regeneration schemes described in the embodiment and Examples 1 and 2 would allow for the transfer of a useful trait to squash plants. Chart 5 summarizes the construction of plasmids which could be used with the Agrobacterium-mediated and microprojectile-mediated gene transfer systems.

| CHART 1 |
| --- |
| Remove Seed Coats, Treat with Clorox, Then Alcohol |
| Germinate Seed For Three to Five days |
| or |
| Obtain Mature Squash Seeds and Treat with Clorox |
| Excise Shoot Apices From Germinating Seedlings |
| Use Prescribed Method to Produce Somatic Embryos |
| or |
| Cut Seeds and Use Prescribed Method to Produce Somatic Embryos |
| Dip Plant Tissues Into Agrobacterium |
| or |
| Bombard Tissues With DNA Coated Microprojectiles |
| Transfer to Culture Plates and Cultivate For Four Days |
| Transfer To Fresh Medium |
| Culture Nine Weeks In Darkness |
| (Can See Callus Growing On Side) |
| Excise Putative Somatic Embryos And Put In Regeneration Media to Produce Plant |

Chart 2

Coat protein gene vectors

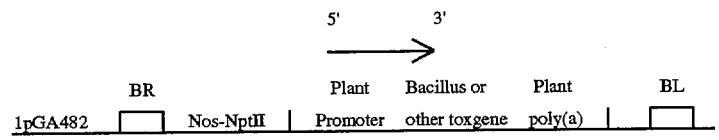

Chart 3

Herbicide gene vectors

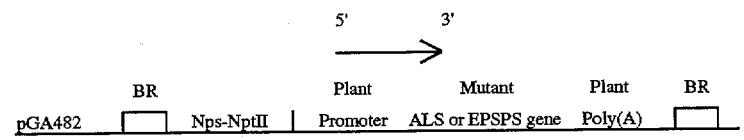

Chart 4

Insect resistance gene vectors

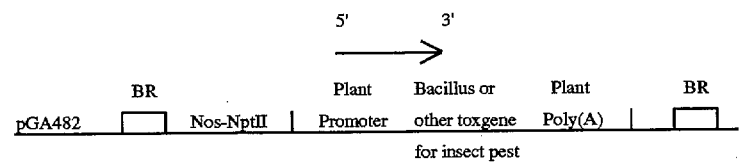

Chart 5

Antimicrobial gene vectors

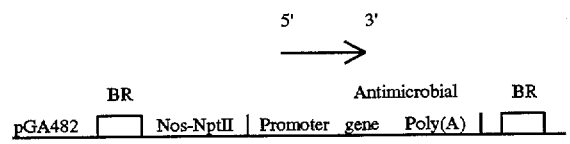

We claim:

1. A method of transforming and regenerating squash plants, which comprises (1) excising shoot tips from germinating squash, (2) transforming embryogenic calli by inoculating the excised squash tissue with Agrobacterium comprising a DNA construct having a beneficial gene and a plant expressible selection marker gene and culturing the resulting explant on an induction media comprising MS media, 2,4,5-T, BAP, and Kn and (3) selectively growing the transformed embryogenic calli on media containing a selection agent for the plant expressible selection marker gene and (4) subjecting the transformed embryogenic calli to an embryogenic regeneration procedure from which whole transformed squash plants can be obtained.

2. A method of transforming and regenerating squash plants, which comprises (1) excising shoot tips from germinating squash seeds, (2) culturing the excised squash tissue on an induction media comprising MS media, 2,4,5-T, BAP, and Kn and introducing foreign DNA having a beneficial gene and a plant expressible selection marker gene into the resulting embryoid tissues by bombardment with microprojectiles and (3) selectively growing the transformed embryogenic calli on media containing a selection agent for the plant expressible selection marker gene and (4) subjecting the transformed embryogenic calli to an embryogenic regeneration procedure from which whole transformed squash plants can be obtained.

3. A method according to claim 1, wherein transformed embryoids are identified by their expression of antibiotic or herbicide resistance.

4. A method of transforming and regenerating squash plants, which comprises (1) excising tissue from mature squash seeds, (2) transforming embryogenic calli by inoculating said excised squash tissue with Agrobacterium comprising a DNA construct having a beneficial gene and a plant expressible selection marker gene and culturing on an induction media comprising MS media, 2,4-D or 2,4,5-T, BAP, and Kn, (3) selectively growing the transformed embryogenic calli on media containing a selection agent for the plant expressible selection marker gene and (4) subjecting the transformed embryogenic calli to an embryogenic regeneration procedure from which whole transformed squash plants can be obtained.

5. A method of transforming and regenerating squash plants, which comprises (1) excising tissue from mature squash seeds, (2) transforming embryogenic calli by culturing the excised squash tissue on an induction media comprising MS media, 2,4-D or 2,4,5-T, BAP, and Kn and introducing foreign DNA having a beneficial gene and a plant expressible selection marker gene into the resulting embryoid by microprojectile bombardment, (3) selectively growing the transformed embryogenic calli on media containing a selection agent for the plant expressible selection marker gene and (4) subjecting the transformed embryogenic calli to an embryogenic regeneration procedure from which whole transformed squash plants can be obtained.

6. A process according to claim 1, wherein the plant expressible selection marker gene is the NPTII gene and the selection agent is kanamycin.

7. A method according to claim 2, wherein transformed embryoids are identified by their expression of antibiotic or herbicide resistance.

8. A method according to claim 4, wherein transformed embryoids are identified by their expression of antibiotic or herbicide resistance.

9. A method according to claim 5, wherein transformed embryoids are identified by their expression of antibiotic or herbicide resistance.

10. A process according to claim 2, wherein the plant expressible selection marker gene is the NPTII gene and the selection agent is kanamycin.

11. A process according to claim 4, wherein the plant expressible selection marker gene is the NPTII gene and the selection agent is kanamycin.

12. A process according to claim 5, wherein the plant expressible selection marker gene is the NPTII gene and the selection agent is kanamycin.

* * * * *